(12) United States Patent
Feenan

(10) Patent No.: US 7,599,728 B2
(45) Date of Patent: Oct. 6, 2009

(54) MAGNETIC RESONANCE IMAGING

(75) Inventor: Peter John Feenan, Witney (GB)

(73) Assignee: General Electric Company, Schenectady, NY (US)

( * ) Notice: Subject to any disclaimer, the term of this patent is extended or adjusted under 35 U.S.C. 154(b) by 147 days.

(21) Appl. No.: 11/396,853

(22) Filed: Apr. 3, 2006

(65) Prior Publication Data

US 2007/0232894 A1    Oct. 4, 2007

(51) Int. Cl.
*A61B 5/05* (2006.01)
(52) U.S. Cl. ...................................... 600/411; 600/415
(58) Field of Classification Search ................ 600/407, 600/410, 427; 324/318; 128/653
See application file for complete search history.

(56) References Cited

U.S. PATENT DOCUMENTS

| | | | | |
|---|---|---|---|---|
| 5,235,281 A | * | 8/1993 | Haragashira et al. | 324/318 |
| 5,329,266 A | * | 7/1994 | Soeldner et al. | 335/216 |
| 5,525,905 A | * | 6/1996 | Mohapatra et al. | 324/318 |
| 5,800,335 A | * | 9/1998 | Koch et al. | 600/22 |
| 5,823,960 A | * | 10/1998 | Young et al. | 600/415 |
| 5,990,681 A | * | 11/1999 | Richard et al. | 324/318 |
| 6,437,568 B1 | * | 8/2002 | Edelstein et al. | 324/318 |
| 6,611,702 B2 | * | 8/2003 | Rohling et al. | 600/415 |
| 6,992,486 B2 | * | 1/2006 | Srinivasan | 324/318 |
| 7,071,638 B2 | * | 7/2006 | Yasui et al. | 318/135 |
| 7,071,692 B2 | * | 7/2006 | Branch et al. | 324/318 |
| 2002/0173717 A1 | * | 11/2002 | Rohling et al. | 600/415 |
| 2004/0015074 A1 | * | 1/2004 | Srinivasan | 600/422 |
| 2004/0075437 A1 | | 4/2004 | Srinivasan | |
| 2005/0034237 A1 | | 2/2005 | Lenting et al. | |
| 2005/0192473 A1 | | 9/2005 | Lonneker-Lammers | |
| 2006/0058683 A1 | * | 3/2006 | Chance | 600/476 |

FOREIGN PATENT DOCUMENTS

EP            468425 A   *  1/1992

* cited by examiner

*Primary Examiner*—Eric F Winakur
*Assistant Examiner*—Michael T Rozanski
(74) *Attorney, Agent, or Firm*—William Baxter; Michael G. Smith; Ellis B. Ramirez

(57) ABSTRACT

A neonate imaging system is provided. The neonate imaging system includes a neonate magnetic resonance imaging system and a mobile neonate incubator system adapted for connection to the neonate magnetic resonance imaging system. The mobile neonate incubator system has an extendable and retractable carriage configured to shuttle the neonate between the mobile neonate incubator system and the neonate magnetic resonance imaging system. A neonate magnetic resonance imaging system is also provided. The neonate magnetic resonance imaging system includes a cylindrical magnet. The cylindrical magnet has a bore with dimensions that approximate dimensions of the neonate. A mobile neonate incubator system is further provided. The mobile neonate incubator system has an extendable and retractable neonate shuttling carriage.

39 Claims, 5 Drawing Sheets

MAGNETIC RESONANCE IMAGING

FIELD OF THE INVENTION

This invention relates generally to magnetic resonance imaging (MRI), and more particularly to techniques for magnetic resonance imaging of neonates.

BACKGROUND OF THE INVENTION

Magnetic resonance imaging (MRI) systems use a strong, homogenous magnetic field to acquire images of a patient. The strength of the magnetic field is typically greater than about 0.5 Tesla, and in many applications can be as high as about three Tesla.

Magnets that produce strong magnetic fields, such as those magnets employed in an MRI system, can also produce a fringe magnetic field that extends beyond the physical confines of the magnet itself. This fringe magnetic field is unwanted, as it attracts ferromagnetic objects, interferes with sensitive electronic equipment and erases data from magnetic storage media.

Most magnets employed in an MRI system are designed to be large enough to accommodate adult-sized patients. However, the larger the magnet, the larger the fringe magnetic field produced.

Newborn babies, also known as neonates, having a medical condition, are placed in specially designed incubators to aid in their development and recovery. These incubators provide a controlled environment for the neonate wherein environmental factors such as temperature, humidity and oxygenation of the atmosphere are regulated. These incubators also commonly have equipment for monitoring the vital functions of the neonate.

Challenges in neonatal care arise when MRI scans of a neonate are needed. In particular, the monitoring equipment in the incubators can be affected by the fringe magnetic field. Further, the fragile nature of the neonates makes them sensitive to movement or handling, beyond that which is necessary, and typically carried out by trained medical personnel who specialize in the particular needs of neonates.

With regard to the fringe magnetic field, some MRI magnet designs employ a set of superconducting coils, separate from the main superconducting coils of the magnet, to actively screen the fringe magnetic field. These screening coils are disposed concentrically and co-axially with the main coils, and are connected to each other in series opposition. The effect of the screening coils is to reduce the strength of the fringe magnetic field.

Even with active screening, there remains a significant fringe magnetic field within certain distances from the magnet center. For example, with a typical MRI magnet having active screening, a fringe magnetic field having a strength of five Gauss can still exist at a distance of as much as 4.5 meters from the magnet center.

Because of the effect the fringe magnetic field has on the neonate monitoring equipment, MRI systems typically are not located within neonatal units. Further, the dimensions and weight of an MRI system typically require that the system be centrally located in a hospital for use by a number of different units. For example, typical MRI magnets are designed with a warm-bore of between about 50 centimeters to about 110 centimeters, e.g., about 90 centimeters, and an overall physical size of nearly 1.5 to two meters in diameter, 1.5 to two meters in length and a weight of four to ten tons.

As a result, MRI systems are generally located within a separate imaging suite and the neonates are transported from the neonatal unit to the imaging suite for scanning. To help minimize the amount of trauma this transporting causes, special incubators have been created to allow the neonate to remain in a controlled environment during transportation and imaging. These special incubators have monitoring equipment that is not affected by a magnetic field.

However, the neonates must still be transferred from their regular incubator to the special incubator, transported to/from the MRI system and then returned to their regular incubator. Thus, this procedure involves extensive movement of the neonate, which can be detrimental to recovery. Further, the special incubator is typically smaller than a regular incubator, which can be restrictive and cause stress for the neonate. Also, any other equipment that accompanies the neonate, such as resuscitation equipment, must also be transported. Therefore, frequent and repeated imagings using this procedure are logistically difficult to arrange.

For the reasons stated above, and for other reasons stated below which will become apparent to those skilled in the art upon reading and understanding the present specification, there is a need in the art for improved techniques for obtaining MRI images of neonates.

BRIEF DESCRIPTION OF THE INVENTION

A neonate imaging system is provided. The neonate imaging system includes a neonate magnetic resonance imaging system and a mobile neonate incubator system adapted for connection to the neonate magnetic resonance imaging system. The mobile neonate incubator system has an extendable and retractable carriage configured to shuttle the neonate between the mobile neonate incubator system and the neonate magnetic resonance imaging system.

A neonate magnetic resonance imaging system is also provided. The neonate magnetic resonance imaging system includes a cylindrical magnet. The cylindrical magnet has a bore with dimensions that approximate dimensions of the neonate.

A mobile neonate incubator system is further provided. The mobile neonate incubator system has an extendable and retractable neonate shuttling carriage.

Systems of varying scope are described herein. In addition to the aspects and advantages described in this summary, further aspects and advantages will become apparent by reference to the drawings and by reading the detailed description that follows.

DETAILED DESCRIPTION OF THE INVENTION

Figure 1:
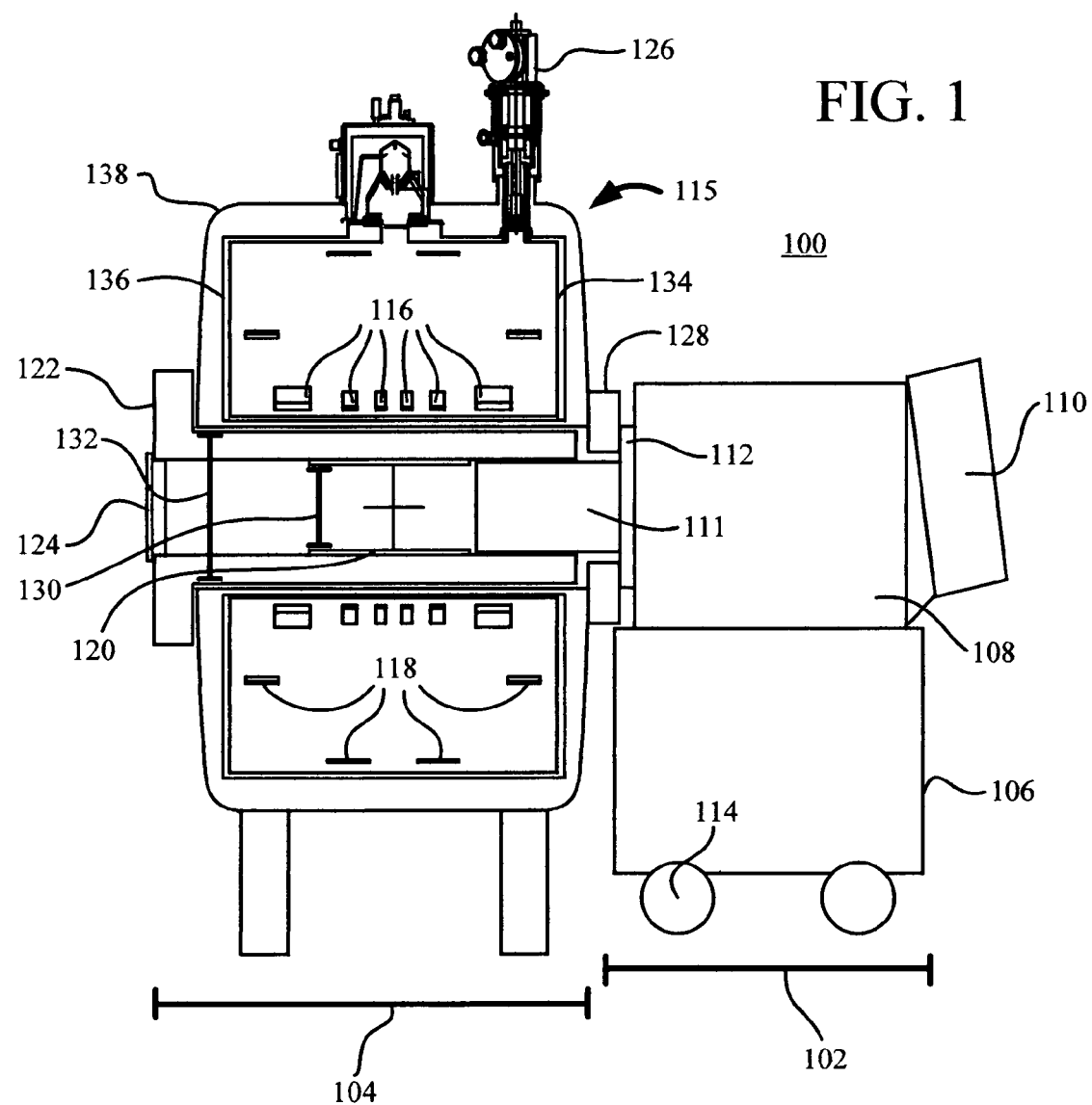
FIG. 1 is a cross-sectional view of an illustrative neonatal imaging system.

Accordingly, a neonate imaging system 100 provides an effective way to obtain medical images of neonates without causing an undue amount of stress or trauma to these fragile and often unstable patients. Specifically, the need for excessive transferring and handling of the neonate, as with conventional practices, is eliminated by neonate imaging system 100 having a mobile neonate incubator system 102. The mobile neonate incubator system 102, which provides a controlled environment, has an extendable and retractable carriage 111 for shuttling the neonate to/from a neonate magnetic resonance imaging (MRI) system 104. MRI system 104 includes compact magnet 115, i.e., having a smaller overall size as compared to a typical full body magnet for adults. Limiting the overall size of magnet 115 reduces the fringe magnetic field produced during operation.

The detailed description is divided into two sections. In the first section, neonate imaging systems are described. In the second section, a conclusion of the detailed description is provided.

Neonatal Imaging Systems

A system that solves the above-stated needs and thus provides for improved MRI imaging of neonates is now described. While the present description is directed to the magnetic resonance imaging of neonates, it is to be understood that the techniques described herein are broadly applicable to a variety of imaging systems and subjects. FIG. 1 is a cross-sectional view of neonate imaging system 100. Neonate imaging system 100 includes mobile neonate incubator system 102 and neonate MRI system 104.

Mobile neonate incubator system 102 includes cart 106, incubator 108, incubator control module 110, neonate carriage 111 and incubator docking connection 112. Cart 106 serves in transporting mobile neonate incubator system 102 to/from neonate MRI system 104. For example, according to an illustrative embodiment, cart 106 includes wheels 114 that allow mobile neonate incubator system 102 to be rolled up to neonate MRI system 104. Cart 106 should be of a height such that when mobile neonate incubator system 102 is rolled up to neonate MRI system 104, incubator docking connection 112 aligns with a corresponding docking connection on neonate MRI system 104, described below. To achieve this alignment, embodiments are anticipated wherein cart 106 has an adjustable height.

Incubator 108 is a controlled environment incubator. Specifically, environmental factors, including, but not limited to, temperature, humidity and oxygenation are controlled within incubator 108. According to an illustrative embodiment, the environmental factors within incubator 108 are controlled by incubator control module 110, described below.

Incubator control module 110, as described above, can control the environmental factors within incubator 108. Incubator control module 110 can also serve to monitor the conditions within incubator 108, as well as, the vital signs of the neonate, for example, as through probes or leads attached to the neonate. Incubator control module 110 can be any conventional PC computer having a central processing unit (CPU), a memory and a user interface, e.g., a screen. Incubator control module 110 can also include an input device, such as keyboard, with which a user can interact with incubator control module 110.

According to an illustrative embodiment, incubator control module 110 is located at a point on mobile neonate incubator system 102 farthest from neonate MRI system 104 (such as is depicted in FIG. 1). This positioning of incubator control module 110 minimizes, or eliminates, the effects of the fringe magnetic field produced by neonate MRI system 104 on incubator control module 110. Therefore, it is not required that incubator control module 110 be specially designed to operate in a magnetic field. However, embodiments are anticipated herein where incubator control module 110 is designed to operate in a magnetic field.

Neonate carriage 111 is an extendable component of mobile neonate incubator system 102. Specifically, when neonate carriage 111 is retracted, neonate carriage 111 is contained within mobile neonate incubator system 102.

In the retracted state, the neonate can be placed in neonate carriage 111. When mobile neonate incubator system 102 is connected to neonate MRI system 104, neonate carriage 111 can then be extended into neonate MRI system 104 for imaging. After imaging is completed, neonate carriage 111 can be retracted back into mobile neonate incubator system 102 for access to the neonate and for transport, e.g., within the neonatal unit.

The environment in neonate carriage 111 is continuous with the environment of mobile neonate incubator system 102, therefore neonate carriage 111 provides the same controlled environment for the neonate as does mobile neonate incubator system 102. Further, since neonate carriage 111, during imaging, is extended into neonate MRI system 104, neonate carriage 111 should not include any metallic materials.

During the extension and retraction of neonate carriage 111, it can be necessary for certain monitoring probes and leads to remain attached to the neonate. As described above, these probes and leads permit incubator control module 110 to monitor the vital signs of the neonate. Thus, extendable connectors, e.g., extendable electrical conduits, can be employed between the probes and leads and incubator control module 110, to accommodate for the extension and retraction of neonate carriage 111. Suitable extendable connectors include, but are not limited to, extendable cords, extendable wiring and extendable piping. Since the probes, leads and extendable connectors are to be used in neonate MRI system 104, each must be configured to operate in a magnetic environment.

Incubator docking connection 112, along with a corresponding connection point on neonate MRI system 104, serve as the connection points between mobile neonate incubator system 102 and neonate MRI system 104. As will be described in detail below, the environments within mobile neonate incubator system 102 and neonate MRI system 104 are equalized prior to scanning, to prevent trauma to the neonate. The connection points can play a role in equalizing the environments. For example, according to an illustrative embodiment, the connection points prevent extension of neonate carriage 111 until the environments are equalized.

The connection points can be further configured such that mobile neonate incubator system 102 and neonate MRI system 104 have to be properly aligned for the connection points to engage. This ensures that neonate carriage 111 is in proper alignment with neonate MRI system 104.

According to an illustrative embodiment, the connection points include a locking mechanism that becomes engaged only when the connection points are properly aligned. Engaging such a locking mechanism serves to prevent unintentional detachment of mobile neonate incubator system 102 from neonate MRI system 104, e.g., during imaging and when neonate carriage 111 is extended.

According to another illustrative embodiment, incubator docking connection 112 is configured to prevent any extension of neonate carriage 111 when mobile neonate incubator system 102 is not connected to neonate MRI system 104. This ensures that neonate carriage 111 is not improperly extended prior to connection, e.g., such as during transport, which may cause injury to the neonate inside.

In an alternative embodiment, neonate carriage 111 is in an extended state before mobile neonate incubator system 102 is mated with MRI system 104. According to this embodiment, mobile neonate incubator system 102 is wheeled up to MRI system 104 and thereby extended neonate carriage 111 is inserted into MRI system 104 for imaging.

MRI system 104 includes magnet 115, radio frequency (RF) coil 120, gradient coil 122, Farady end cap 124, cryocooler 126 and MRI system connection 128. Magnet 115 is a compact superconducting magnet that includes multiple main magnetic field-producing coils 116 and multiple screening coils 118. According to an illustrative embodiment, magnet 115 is a compact three Tesla superconducting magnet.

It is to be understood that FIG. 1 is a cross-sectional representation. Namely, magnet 115 has a cylindrical shape and main magnetic field-producing coils 116/screening coils 118 form concentric circles around a central lateral core.

In magnet 115, main magnetic field-producing coils 116 and screening coils 118 are surrounded by coil vessel 134. Coil vessel 134 can be composed of any suitable metallic material, including, but not limited to, stainless steel. Coil vessel 134 typically contains liquid helium. Thus, according to an illustrative embodiment, coil vessel 134 is a stainless steel helium vessel.

Coil vessel 134 is surrounded by thermal shield 136. Thermal shield 136 can be composed of any suitable thermal shielding material, including, but not limited to, aluminum. Thermal shield 136 is surrounded by outer vacuum container 138. Outer vacuum container 138 can be composed of any suitable metallic material, including, but not limited to, stainless steel.

Cryocooler 126 is connected to magnet 115. According to an illustrative embodiment, cryocooler 126 is a two-stage cryocooler, having a first stage connected to thermal shield 136 and a second stage attached to a recondenser (not shown). The connection of a two-stage cryocooler to an MRI system is well known to those in the art and is not further described herein.

The configuration shown in FIG. 1 provides a cryogenic environment for magnet 115 that is adapted for zero boil-off of the liquid helium. Specifically, magnet 115 is superconducting and should be kept at about 4.2 degrees Kelvin to remain superconducting. While thermal shield 136 prevents most of the heat from the external environment from entering coil vessel 134, invariably some heat gets past thermal shield 136 and into coil vessel 134. This unwanted heat can cause the liquid helium within coil vessel 134 to "boil away," i.e., as a gas. Cryocooler 126, however, takes that gas and recondenses that gas back into a liquid, e.g., by cooling the gas. Therefore, substantially none of the helium escapes.

During operation of neonate MRI system 104, main magnetic field-producing coils 116 produce a fringe magnetic field. This fringe magnetic field, if not controlled or reduced, can adversely affect components of mobile neonate incubator system 102. Namely, as mentioned above, a fringe magnetic field can attract ferromagnetic objects, interfere with sensitive electronic equipment and erase data from magnetic storage media. Screening coils 118 serve to actively screen the fringe magnetic field so as to prevent the fringe magnetic field from adversely affecting any of the components of mobile neonate incubator system 102 when mobile neonate incubator system 102 is connected to neonate MRI system 104. Configurations of the fringe magnetic fringe field produced by neonate MRI system 104 will be described in detail below.

The size of magnet 115 defines the dimensions of a magnet bore 132 in the center thereof. As described above, magnet 115 is a compact magnet meaning that the size of magnet 115 is chosen so as to define magnet bore 132 having dimensions that, in conjunction with the dimensions of gradient coil 122 (given below) therein, approximate the dimensions of a neonate. For example, magnet 115 can define a magnet bore 132 having a size, as defined by its diameter, of between about 30 and about 50 centimeters, for example, from between about 35 centimeters and about 45 centimeters. Limiting the overall size of magnet 115 reduces the fringe magnetic field produced during operation.

Gradient coil 122 lies within magnet bore 132. Gradient coil 122 enables spatial localization of the imaging signal. The dimensions of gradient coil 122, along with RF coil 120 therein, define an inner cavity 130 of neonate MRI system 104. As will be described in detail below, inner cavity 130 is designed to be only large enough to accept neonate carriage 111 therein. For example, according to an illustrative embodiment, inner cavity 130 has a size, as defined by its diameter, of between about 25 centimeters and about 40 centimeters. The function of a gradient coil is well known to those in the art and is not further described herein.

The surfaces, e.g., inner surfaces, of gradient coil 122 can be coated with an acoustic noise reduction material to reduce the amount of noise experienced by the neonate during scanning. A reduced amount of noise will serve to minimize the trauma to the neonate. Suitable acoustic noise reduction materials include, but are not limited to, foam or any other conventional noise reduction material.

RF coil 120 lies within gradient coil 122. RF coil 120 transmits energy, or resonance, and receives signal information. The function of an RF coil is well known to those in the art and is not further described herein.

Faraday end cap 124 serves in forming a Faraday cage for scanning. Specifically, a rear bulkhead of neonate carriage 111, as will be described in detail below, in combination with end cap 124 form a Faraday cage within magnet bore 132.

As discussed above, incubator docking connection 112 forms a connection with a complimentary connection on neonate MRI system 104, e.g., MRI system connection 128. As described above, the connection between incubator docking connection 112 and MRI system connection 128 can be a locking connection so as to prevent unintentional separation of mobile neonate incubator system 102 from neonate MRI system 104 during scanning. However, due to the fragile nature of the neonates being scanned, the locking mechanism should contain an override component that permits a user to actively unlock and separate the mobile neonate incubator system 102 from neonate MRI system 104, at any point.

Further, incubator docking connection 112/MRI system connection 128 can also provide electrical connections between sensor(s), located within magnet 115, and incubator control module 110. These sensors permit incubator control module 110 to monitor the environmental factors within magnet 115. Sensors that can be located within magnet 115, include, but are not limited to, temperature sensors, humidity sensors and oxygen sensors. These sensors should be configured to operate in a magnetic environment.

Since the size of neonate MRI system 104 is scaled down to the dimensions of a neonate, neonate MRI system 104 can more easily be located in the neonatal unit of a hospital without the same concerns for space that are common with MRI systems for adults. For example, a neonate MRI system can be located in special care baby units (SCBUs) or in neonatal infant care units (NICUs). Further, the placement of a neonate MRI system within a neonatal unit minimizes the amount of movement the fragile neonates are exposed to when MRI images are needed.

Neonate MRI system 104, similar to mobile neonate incubator system 102, can have a controlled environment, so as to limit trauma to the neonate during scanning. For example, environmental factors, including, but not limited to, temperature, humidity and oxygenation, can be controlled within neonate MRI system 104. According to an illustrative embodiment, the environmental factors within neonate MRI system 104 are controlled by incubator control module 110. Specifically, once mobile neonate incubator system 102 is connected to neonate MRI system 104 a continuous environment is formed between magnet bore 132 and incubator 108. Incubator control module 110 can then regulate and monitor this continuous environment. Once the environmental factors within the continuous environment are uniform, neonate carriage 111 can then be extended into neonate MRI system 104 for imaging.

Additionally, to regulate the temperature within magnet bore 132, gradient coil 122 can be cooled. For example, during imaging, high current (e.g., having a square-wave shape of rise-time of about 100 microseconds) is pulsed through gradient coil 122. This current pulse causes gradient coil 122 to vibrate. To prevent excessive vibration, gradient coil 122 is typically encased in an epoxy resin. The epoxy resin is rigid and serves to minimize movement of gradient coil 122. Cooling pipes can be incorporated in the epoxy resin, proximate to gradient coil 122, and serve to cool gradient coil 122.

The cooling pipes can be made of copper and contain a suitable cooling fluid. Suitable cooling fluids include, but are not limited to, water.

Alternatively, a water-cooling jacket can be located within an inside surface, i.e., within the bore of, gradient coil 122. Like the cooling pipes described above, the water-cooling jacket can serve to remove heat from gradient coil 122.

Magnet 115 can also include a viewing window (not shown) into magnet bore 132 for visually monitoring the neonate during imaging. According to this illustrative embodiment, at least a portion of neonate carriage 111 is composed of a clear material, such as a clear plastic material, that permits viewing through a viewing window in magnet 115 and into neonate carriage 111.

Alternatively, other means of visually monitoring the neonate during scanning can be employed. By way of example only, a camera adapted for use in the presence of a magnetic field can be employed. The images captured by the camera can be displayed on a screen visible to the user. Further, fiber optic visual systems can be employed to monitor the neonate. Suitable fiber optic visual systems currently exist, and include those used to examine orifices of the body. Additionally, mirror systems may be similarly implemented. For example, mirrors may be positioned to provide a clear line-of-sight path from the neonate to the user.

Being able to visually monitor the neonate during scanning is important, as the condition of a neonate is typically unstable. Thus, for example, if the user is visually monitoring the neonate and sees that the neonate, e.g., stops breathing, the user can intervene immediately to stop the scan.

Images resulting from scans of the neonate can then be displayed on a user interface (not shown), e.g., a screen, as with conventional MRI scans. The operations involved in scanning and displaying images of a patient using an MRI system are well known to those in the art and are not described further herein.

Figure 2:
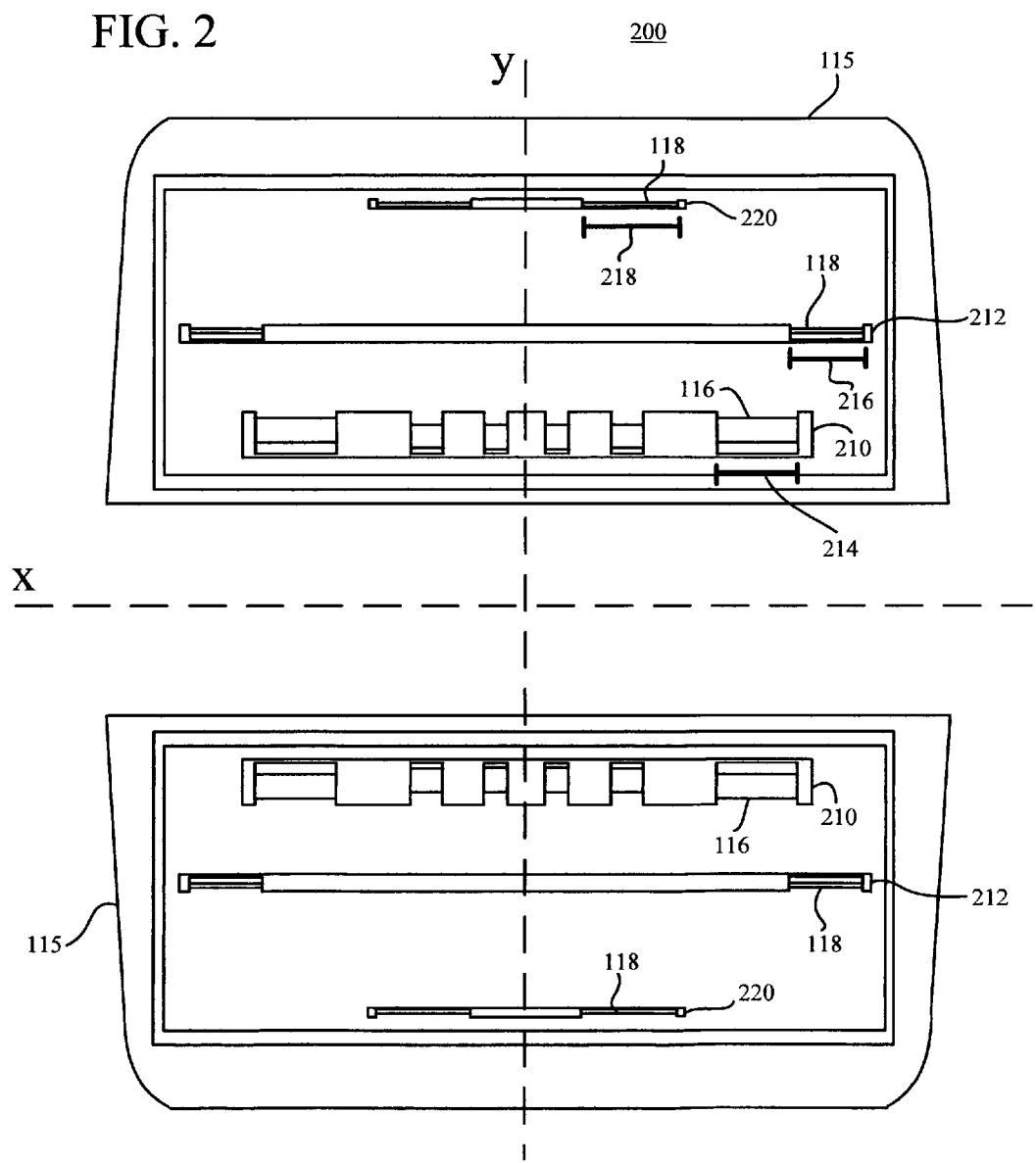
FIG. 2 is a diagram of an illustrative coil configuration.

FIG. 2 is a cross-sectional view of an illustrative configuration 200 of main magnetic field-producing coils 116 and screening coils 118 that can be implemented in magnet 115. Some components associated with magnet 115, including components shown in FIG. 1, have been intentionally left out of FIG. 2 for ease of description. Further, as with FIG. 1, the depiction in FIG. 2 is a cross-sectional view and it is to be understood that magnet 115, and all components thereof, are continuous. For example, main magnetic field-producing coils 116 form continuous coils around a continuous cylindrical inner former structure 210 (described below).

Main magnetic field-producing coils 116 are wound around inner former structure 210. Inner former structure 210 can be composed of any material having suitable mechanical properties at low operating temperatures, including, but not limited to, one or more of fiber-glass, stainless steel and aluminum. Inner former structure 210 is designed to provide a winding surface for main magnetic field-producing coils 116. Specifically, inner former structure 210 is configured to have a number of coil pockets 214 into which main magnetic field-producing coils 116 can be wound. As shown in FIG. 2, inner former structure 210 has six coil pockets 214.

Screening coils 118 are wound around outer former structures 212 and 220. Similar to inner former structure 210, outer former structures 212 and 220 can be composed of any material having suitable mechanical properties at low operating temperatures, including, but not limited to, one or more of fiber-glass, stainless steel and aluminum. Outer former structures 212 and 220 are designed to provide winding surfaces for screening coils 118. Specifically, outer former structure 212 is configured to have a number of coil pockets 216 and outer former structure 220 is configured to have a number of coil pockets 218 into which screening coils 118 can be wound. As shown in FIG. 2, outer former structure 212 and outer former structure 220 have two coil pockets 216 and two coil pockets 218, respectively. The fabrication of main magnetic field-producing coils and screening coils around former structures in MRI magnets is well known to those in the art and is not further described herein.

The positioning of the coil pockets, namely coil pockets 214, 216 and 218, relative to each other, is a design consideration. For example, as shown in FIG. 2, the placement of coil pockets 216 in outer former structure 212 relative to the placement of coil pockets 218 in outer former structure 220 results in screening coils 118 being in a closer proximity to main magnetic field-producing coils 116 at either end of magnet 115, i.e., along the x-axial direction. Further, the placement of coil pockets 216 in outer former structure 212 relative to the placement of coil pockets 218 in outer former structure 220 results in screening coils 118 being relatively farther from main magnetic field-producing coils 116 at the center of magnet 115, e.g., at the x-axial center.

As shown in FIG. 2, outer former structures 212 and 220 each have a plurality of coil pockets therein. Specifically, a pair of coil pockets 216 and a pair of coil pockets 218 are present in outer former structures 212 and 220, respectively. This configuration results in the placement of two sets of screening coils 118 in magnet 115, each set having two screening coils 118. Thus, according to an illustrative embodiment, magnet 115 has greater than two screening coils 118, for example, two pairs of screening coils 118, i.e., for a total of four screening coils 118.

As further shown in FIG. 2, when screening coils 118 occur in sets, the sets can be placed at different radial positions relative to one another. Namely, since the components of magnet 115, such as the former structures, are cylindrical, radial positions are defined as positions extending out a certain distance from the center of the cylinder. Thus, for example, outer former structure 220 extends out along the y-axial direction a greater distance from the y-axial center of magnet 115 than does outer former structure 212. Therefore, outer former structures 212 and 220 are at different radial positions relative to one another, resulting in screening coils 118 being positioned at different radial positions relative to one another.

Another consideration is the positioning of screening coils 118 relative to main magnetic field-producing coils 116. According to one illustrative embodiment, the axial extent of screening coils 118 is greater than the axial extent of main magnetic field-producing coils 116. FIG. 2 depicts such a configuration. Specifically, the positioning of coil pockets 216 and 218 relative to the positioning of coil pockets 214 places screening coils 118 at a greater distance from the center of magnet 115 than main magnetic field-producing coils 116, both along the x-axial and the y-axial directions, i.e., at a greater axial extent.

The widths of the coil pockets, i.e., the number of turns of wire the coil pockets contain, and the spacing between the coil pockets are also design considerations. For example, the coil pockets 214 in inner former structure 210 nearer the center of magnet 115 have widths that are less than the widths of coil pockets 214 in inner former structure 210 towards the ends of magnet 115. Further, coil pockets 214 in inner former structure 210 nearer the center of magnet 115 are grouped closer to each other relative to coil pockets 214 in inner former structure 210 towards the ends of magnet 115.

Figure 3:
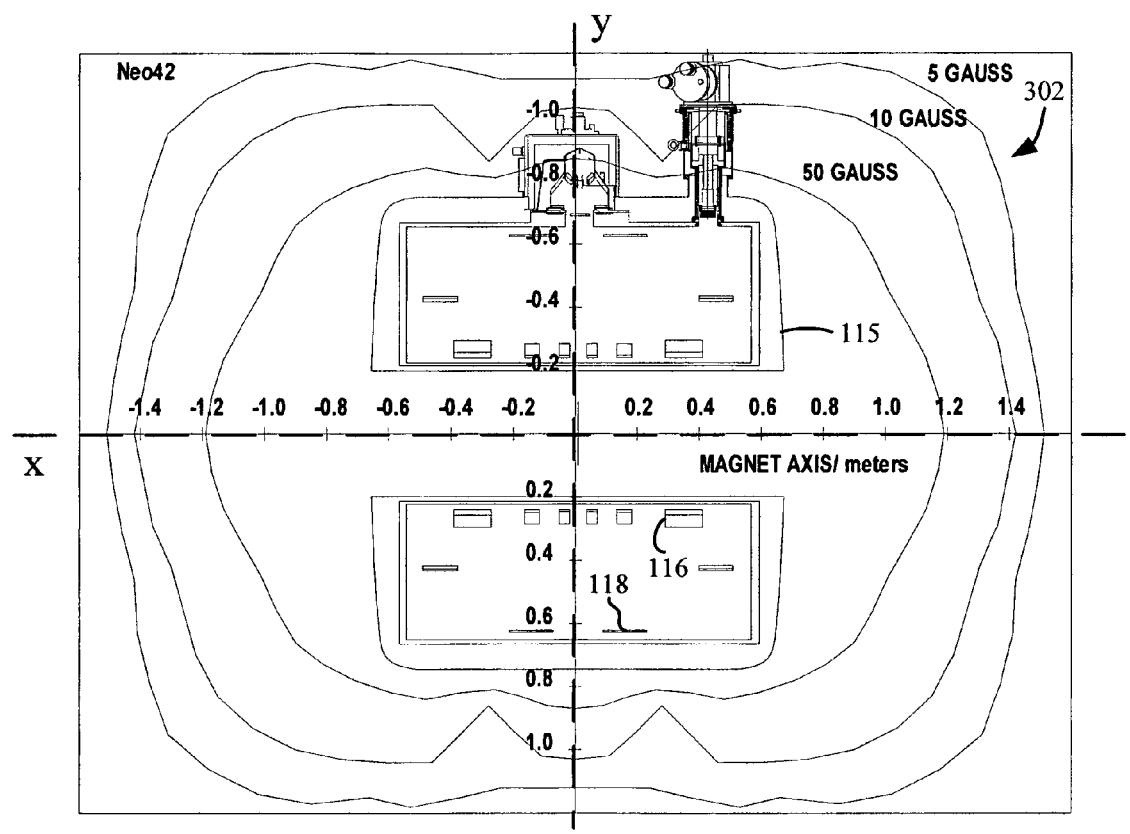
FIG. 3 is a diagram of an illustrative fringe magnetic field produced by a neonate magnetic resonance imaging (MRI) system.

FIG. 3 is a diagram of an illustrative fringe magnetic field 302 produced by neonate MRI system 104. Fringe magnetic field 302, which is produced by magnet 115, is ellipsoidal in shape, i.e., extending a greater distance in the x-axial direction than in the y-axial direction from the center of magnet 115.

Fringe magnetic field 302 decreases in strength as the distance from magnet 115 increases. For example, fringe magnetic field 302 has a strength of about 50 Gauss at a distance of about 1.2 meters in the x-axial direction from the x-axial center of magnet 115 and about 0.8 meters in the y-axial direction from the y-axial center of magnet 115. Fringe magnetic field 302 decreases in strength to about 10 Gauss at a distance of about 1.4 meters in the x-axial direction from the x-axial center of magnet 115 and about one meter in the y-axial direction from the y-axial center of magnet 115. Finally, fringe magnetic field 302 has a strength of about five Gauss at a distance of about 1.5 meters in the x-axial direction from the x-axial center of magnet 115 and 1.1 meters in the y-axial direction from the y-axial center of magnet 115.

Further, as described above, the components of magnet 115, such as the former structures, are cylindrical and radial positions are defined as positions extending out a certain distance from the center of the cylinder. Therefore, the radial extent of fringe magnetic field 302 can also be measured. In the case of an ellipsoidal fringe magnetic field, the radial extent is roughly equivalent to the y-axial extent of the fringe magnetic field.

Figure 4:
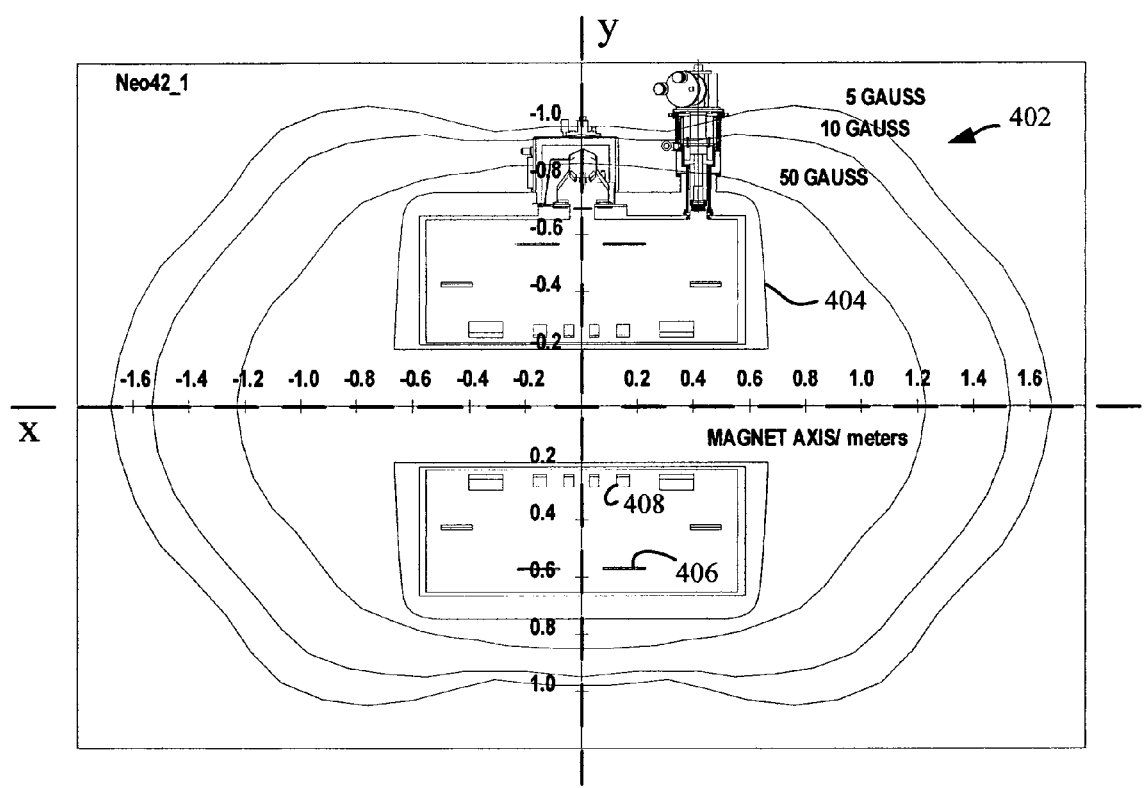
FIG. 4 is a diagram of another illustrative fringe magnetic field produced by a neonate MRI system.

With a fringe magnetic field having the shape of fringe magnetic field 302, the total resultant magnetic field in the magnet bore is three Tesla, where the field uniformity is better than five parts per million within a roughly spherical volume of diameter 20 cm. Reference to FIG. 4, will show that the shape of the fringe magnetic field can be altered by changing the configuration of the coils in the MRI magnet.

FIG. 4 is a diagram of an illustrative fringe magnetic field 402 that can be produced by changing the configuration of the coils in the MRI magnet. Like fringe magnetic field 302, described above, fringe magnetic field 402 produced by magnet 404 is ellipsoidal in shape. However, fringe magnetic field 402 extends out a greater distance in the x-axial direction and a lesser distance in the y-axial direction from the center of magnet 404, as compared with fringe magnetic field 302 produced by magnet 115.

As with fringe magnetic field 302, described above, fringe magnetic field 402 decreases in strength as the distance from magnet 404 increases. For example, fringe magnetic field 402 has a strength of about 50 Gauss at a distance of about 1.2 meters in the x-axial direction from the x-axial center of magnet 404 and about 0.8 meters in the y-axial direction from the y-axial center of magnet 404. Fringe magnetic field 402 decreases in strength to about 10 Gauss at a distance of about 1.5 meters in the x-axial direction from the x-axial center of magnet 404 and about 0.9 meters in the y-axial direction from the y-axial center of magnet 404. Finally, fringe magnetic field 402 has a strength of about five Gauss at a distance of about 1.7 meters in the x-axial direction from the x-axial center of magnet 404 and about one meter in the y-axial direction from the y-axial center of magnet 404.

As described above, the shape of the fringe magnetic field can be altered by changing the configuration of the MRI magnet. Specifically, the position and/or number of coils in the main magnetic field-producing coils and/or screening coils (e.g., main magnetic field-producing coils 116/screening coils 118), can be varied to alter the shape of the fringe magnetic field. For example, either fringe magnetic field 302 or fringe magnetic field 402 can be obtained by different positionings of the screening coils, as shown in FIGS. 3 and 4. By way of example only, the central set of screening coils 406 in FIG. 4 have been moved closer to the y-axial center in magnet 404 (as compared to screening coils 118 in FIG. 3), and hence closer to main magnetic field-producing coils 408. Further, fringe magnetic fields having other shapes can be obtained. For example, a fringe magnetic field having a spheroidal shape can be similarly obtained.

A desired shape of the fringe magnetic field can be based, at least in part, on where the MRI system is going to be located. As described above, fringe magnetic field 402 has a smaller radial extent than fringe magnetic field 302. If, for example, the MRI system is going to be situated in the center of a room with electronic equipment on either side of the magnet, i.e., at radial positions from the center of the magnet, then a fringe magnetic field having the shape of fringe magnetic field 402 will be less likely to affect the equipment. Alternatively, if the MRI system is going to be situated in a room with electronic equipment in front of, or behind, i.e., along the x-axial direction of the magnet, then a fringe magnetic field having the shape of fringe magnetic field 302, will be less likely to affect the equipment.

In the case where mobile neonate incubator system 102 is transported towards, or away from, neonate MRI system 104 along an x-axial direction to the magnet, fringe magnetic field 302, will be less likely to affect incubator control module 110 than fringe magnetic field 402. With a fringe magnetic field of five Gauss or less, most electronic equipment is not affected.

Figure 5:
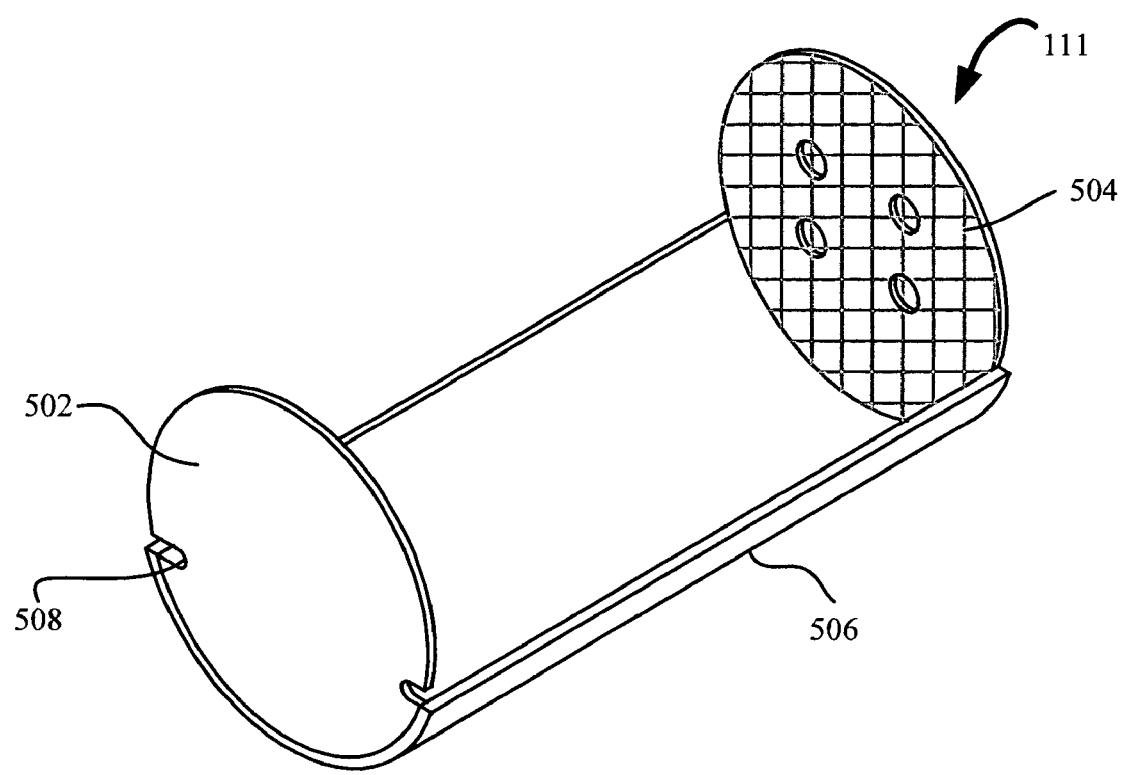
FIG. 5 is a diagram of an illustrative neonate carriage.

FIG. 5 is a diagram of illustrative neonate carriage 111. Neonate carriage 111 includes front bulkhead 502, rear bulkhead 504 and carriage support 506 extending therebetween.

Neonate carriage 111 is oriented in mobile neonate incubator system 102 such that, during operation, front bulkhead 502 is the first component of neonate carriage 111 to enter magnet bore 132 of magnet 115. Front bulkhead 502 can have slots 508 that mate with rails affixed to magnet 115 proximate to magnet bore 132. Slots 508 sliding along these rails can help support neonate carriage 111 in an extended position and prevent neonate carriage 111 from twisting within magnet bore 132.

Carriage support 506 has a shape, size and contour that are suitable for supporting a neonate. For example, carriage support 506 has a length that approximates the length of a neonate. Further, carriage support 506 can have low aspect sides that make access to the neonate easier. However, carriage support 506 should sufficiently surround the neonate to prevent injury by accidental contact of the neonate with the surfaces of magnet bore 132, e.g., during extension or retraction of neonate carriage 111.

During operation, rear bulkhead 504 is the last component of neonate carriage 111 to enter magnet bore 132 of magnet 115. Rear bulkhead 504 can have a Faraday shield on a surface thereof facing front bulkhead 502. The Faraday shield in conjunction with Faraday end cap 124 (described above) form a Faraday cage for scanning.

Rear bulkhead 504 can include one or more openings or feedthroughs, through which probes or leads attached to the neonate can pass to incubator control module 110. Further, any conduits to life support equipment for the neonate can similarly pass through these openings.

CONCLUSION

Neonatal imaging systems have been described. Although specific embodiments are illustrated and described herein, any arrangement which is calculated to achieve the same purpose may be substituted for the specific embodiments shown. This application is intended to cover any adaptations or variations. For example, although described in medical imaging terms, it should be appreciated that implementations can be made in an industrial or any other secured environment that provides the required relationships.

In particular, the names of the components of the systems are not intended to limit embodiments. Furthermore, additional components can be added to the systems, functions can be rearranged among the components, and new components to correspond to future enhancements and physical devices used in embodiments can be introduced without departing from the scope of embodiments. Embodiments are applicable to future medical devices, different imaging systems, and new data types.

The terminology used in this application with respect to the neonate imaging technology is meant to include all data objects and network environments and alternate technologies that provide the same functionality as described herein.

I claim:

1. A neonate imaging system comprising:
a neonate magnetic resonance imaging system; and
a mobile neonate incubator system having a continuous, controlled environment adapted for connection to the neonate magnetic resonance imaging system through an incubator docking connection and adapted for separation from the neonate magnetic resonance imaging system, the mobile neonate incubator system having an extendable and retractable carriage configured to shuttle a neonate between the mobile neonate incubator system and the neonate magnetic resonance imaging system,
wherein the mobile neonate incubator system, when connected to the neonate magnetic resonance imaging system, has the continuous, controlled environment with the neonate magnetic resonance imaging system.

2. The system of claim 1, wherein the neonate magnetic resonance imaging system has dimensions scaled to dimension of the neonate.

3. The system of claim 1, further comprising a cart for transporting the mobile neonate incubator system to the neonate magnetic resonance imaging system.

4. The system of claim 1, wherein the neonate magnetic resonance imaging system and the mobile neonate incubator system have complementary mating connection points that align with each other when the neonate magnetic resonance imaging system and the mobile neonate incubator system align.

5. The system of claim 4, wherein the complementary mating connection points comprise a locking mechanism that engages when the complementary mating connection points align with each other.

6. The system of claim 4, wherein extension of the carriage is prevented prior to alignment of the complementary mating connection points with each other.

7. The system of claim 1, further comprising an incubator control module that includes one or more probes, leads, and sensors to monitor neonate condition and condition of the controlled environment.

8. The system of claim 1, further comprising a monitoring system for visually monitoring the neonate.

9. The system of claim 8, wherein the monitoring system is one or more of a camera-based monitoring system, a mirror-based monitoring system and a fiber optic-based monitoring system.

10. A neonate magnetic resonance imaging system comprising:
a housing;
a cylindrical magnet inside the housing, the cylindrical magnet having a bore with dimensions that approximate dimensions of the neonate; and
an incubator docking connection on the housing and having at least one connection point that is operable to prevent insertion of a neonate carriage into the bore, the at least one connection point operable to prevent extension of the neonate carriage until a closed, controlled environment of the neonate carriage is equalized with a closed, controlled environment of the neonate magnetic resonance imaging system.

11. The system of claim 10, wherein the magnet is a superconducting magnet.

12. The system of claim 10, wherein the magnet is a three Tesla superconducting magnet.

13. The system of claim 10, wherein the bore has a diameter of between about 30 and about 50 centimeters.

14. The system of claim 10, wherein the bore has a diameter of between about 35 and about 45 centimeters.

15. The system of claim 10, wherein the magnet has a plurality of main magnetic field-producing coils and a plurality of screening coils.

16. The system of claim 15, wherein the magnet has more than two screening coils.

17. The system of claim 15, wherein the magnet has four screening coils.

18. The system of claim 15, wherein the superconducting magnet produces a fringe magnetic field that has strength of about five Gauss at a distance of about 1.5 meters in an x-axial direction from an xaxial center of the magnet and 1.1 meters in a yaxial direction from a yaxial center of the magnet.

19. The system of claim 15, wherein the superconducting magnet produces a fringe magnetic field that has a strength of about five Gauss at a distance of about 1.7 meters in an x-axial direction from an x-axial center of the magnet and about one meter in a y-axial direction from a y-axial center of the magnet.

20. The system of claim 10, further comprising a gradient coil.

21. The system of claim 20, wherein the gradient coil defines an inner cavity of the magnet.

22. The system of claim 20, wherein one or more surfaces of the gradient coil are coated with an acoustic noise reduction material.

23. The system of claim 20, wherein the gradient coil has a cooling component associated therewith.

24. A system comprising:
a neonate magnetic resonance imaging system;
a mobile neonate incubator system having a continuous, controlled environment having an extendable and retractable neonate shuttling carriage and having an incubator docking connection, the incubator docking connection having complementary mating connection points to the neonate magnetic resonance imaging system, the incubator docking connection adapted for separation from the neonate magnetic resonance imaging system, the carriage configured to shuttle a neonate between the mobile neonate incubator system and the neonate magnetic resonance imaging system, wherein the mobile neonate incubator system, when connected to the neonate magnetic resonance imaging system, has the continuous, controlled environment with the neonate magnetic resonance imaging system.

25. The system of claim 24, wherein environmental factors within the mobile neonate incubator system are regulated.

26. The system of claim 25, wherein the environmental factors are one or more of temperature, humidity and oxygenation.

27. The system of claim 24, further comprising an incubator control module adapted to regulate environmental factors within the mobile neonate incubator system.

28. The system of claim 24, further comprising an incubator control module adapted to monitor conditions within the mobile neonate incubator system.

29. The system of claim 24, further comprising an incubator control module adapted to monitor one or more vital signs of the neonate.

30. The system of claim 24, wherein the shuttling carriage comprises:
a front bulkhead;
a rear bulkhead; and
a carriage support extending between the front bulkhead and the rear bulkhead.

31. The system of claim 30, wherein the rear bulkhead comprises a Faraday shield on a surface thereof facing the front bulkhead.

32. A combined closed environment and imaging apparatus comprising:
an imaging system having an imaging bore and configured to acquire diagnostic imaging data of a medical patient; and
a mobile carrier having a docking connection that is adapted for connection to the imaging system and adapted for separation from the imaging system, the mobile carrier configured to shuttle a neonate to and from the imaging system, the mobile carrier supporting a continuous closed environment patient housing that is configured to allow placement of the continuous closed environment patient housing in the imaging bore without removal of the continuous closed environment patient housing from the mobile carrier, the continuous closed environment patient housing being operable to equalize the continuous closed environment in the continuous closed environment patient housing with another closed environment.

33. The combined apparatus of claim 32 wherein the mobile carrier includes an extendable and retractable carriage operably connected to extend and retract the closed environment patient housing to and from the imaging bore.

34. The combined apparatus of claim 32 wherein the imaging system is a magnetic resonance imaging system.

35. The combined apparatus of claim 32 wherein the closed environment housing is sized to receive a neonate.

36. The combined apparatus of claim 32 wherein the imaging system and mobile carrier have complimentary mating connection points that align with each other when the imaging system and mobile carrier align, and wherein placement of the closed environment housing in the imaging bore is prevented if the complimentary connection points are misaligned.

37. A neonatal incubator comprising:
a mobile carrier;
a docking connection; and
a neonate carriage providing a controlled environment for a neonate and supported by the mobile carrier, the neonate carriage extendable and retractable into a controlled environment of an imaging bore of a medical scanner to allow imaging of a neonate without removal of the neonate carriage from the mobile carrier, the neonate carriage operable to shuttle a neonate into the controlled environment of the medical scanner, the neonate carriage being operable to equalize the controlled environment of the neonate carriage with the controlled environment of the medical scanner and have a continuous controlled environment with the controlled environment of the medical scanner.

38. The incubator of claim 37 wherein the neonate carriage is absent of metallic materials.

39. The incubator of claim 37 further comprising an incubator control module that includes one or more probes, leads, and sensors to monitor neonate condition and condition of the continuous controlled environment.

* * * * *

UNITED STATES PATENT AND TRADEMARK OFFICE
CERTIFICATE OF CORRECTION

PATENT NO. : 7,599,728 B2
APPLICATION NO. : 11/396853
DATED : October 6, 2009
INVENTOR(S) : Feenan It is certified that error appears in the above-identified patent and that said Letters Patent is hereby corrected as shown below:

Col. 12
In claim 18, line 51 "direction from an xaxial center of the magnet and 1.1 meters" should be corrected to "direction from an x-axial center of the magnet and 1.1 meters"

Col. 12
In claim 18, line 52 "in a yaxial direction from a yaxial center of the magnet" should be corrected to "in a y-axial direction from a yaxial center of the magnet"

Signed and Sealed this

Twenty-third Day of March, 2010

David J. Kappos
*Director of the United States Patent and Trademark Office*